United States Patent [19]
Chisdes

[11] 3,964,999
[45] June 22, 1976

[54] DETERMINATION OF SODIUM FORM WATER SOFTENER BREAKTHROUGH

[75] Inventor: David M. Chisdes, Wayne, N.J.

[73] Assignee: Beckman Instruments, Inc., Fullerton, Calif.

[22] Filed: Apr. 11, 1975

[21] Appl. No.: 567,367

Related U.S. Application Data

[63] Continuation of Ser. No. 398,662, Sept. 19, 1973, abandoned.

[52] U.S. Cl. ............................ 210/23 R; 210/25; 210/96 R; 210/321 R
[51] Int. Cl.² ........................................ B01D 13/00
[58] Field of Search .................. 210/96, 301, 23, 25

[56] References Cited
UNITED STATES PATENTS

| | | | |
|---|---|---|---|
| 2,617,766 | 11/1952 | Emmett et al. | 210/25 |
| 3,383,310 | 5/1968 | Ammer | 210/96 X |
| 3,398,091 | 8/1968 | Greatorex | 210/23 |
| 3,495,943 | 2/1970 | Kapff | 210/96 |
| 3,639,231 | 2/1972 | Bresler | 210/23 |
| 3,768,649 | 10/1973 | Fleckenstein | 210/96 |

*Primary Examiner*—John Adee
*Attorney, Agent, or Firm*—R. J. Steinmeyer; P. R. Harder

[57] ABSTRACT

Detection of exhaustion of sodium form water softeners is accomplished by subjecting sample of the outflow from a water softener to reverse osmosis in order to separate monovalent (sodium) and divalent (hardness or magnesium and calcium) ions differentially from the outflow and measuring conductivity before and after the reverse osmosis. The two conductivities are compared in a ratiometer or differential device. After the softener becomes exhausted the divalent ion concentration in the outflow increases. Consequently the conductivity ratio changes to indicate that the water softener has become exhausted.

15 Claims, 2 Drawing Figures

DETERMINATION OF SODIUM FORM WATER SOFTENER BREAKTHROUGH

This is a continuation of application Ser. No. 398,662, filed Sept. 19, 1973 now abandoned.

BACKGROUND OF THE INVENTION

In water softening, utilizing the zeolite or ion exchange process, divalent or hardness, calcium and magnesium ions are replaced by monovalent ions. In the case of a sodium form water softener the hardness ions are replaced by sodium ions. This leaves a product water or outflow from the water softener that has a very slight conductivity difference from the hard water feed. The problem is compounded if the feed has a high sodium ion background, as the conductivity differences between product and feed will be minute.

The renders difficult the detection of water softener exhaustion by merely measuring the conductivity of the effluent.

It is accordingly an object of the invention to provide a system for detecting exhaustion of a water softener and controlling the regeneration thereof which does not depend upon high degree of sensitivity in the measurement of product conductivity or continuous recalibration under various conditions of operation which would be necessary in the utilization of highly sensitive conductivity measurement instruments.

Other and further objects, features and advantages will become apparent as the description proceeds.

SUMMARY OF THE INVENTION

In carrying out the invention in accordance with a preferred form thereof the softened water product or outflow from a water softener is subjected to means for discriminating between monovalent and divalent ions. This is done by differentially rejecting monovalent and divalent ions from the product. Differential rejection is preferably done by means of a reverse osmosis unit.

Then conductivity is measured both before and after the product has flowed through the reverse osmosis unit, and the two conductivities are compared. When the water softener has become exhausted the difference between the two conductivities becomes much greater and an indication of water softener exhaustion is provided. The conductivities are in the ratio 10:1 when the softener is functional, and increase to higher value, e.g. 100:1 when the softener has become exhausted.

A better understanding of the invention will be afforded by the following detailed description considered in conjunction with the accompanying drawing in which:

FIG. 1 is a schematic diagram of an embodiment of the invention for indicating exhaustion of a sodium type water softener column; and FIG. 2 is a schematic diagram of a modification in the apparatus of FIG. 1 illustrating the manner in which the detection system is employed for automatically effecting regeneration of a water softener column.

Like reference characters are utilized throughout the drawing to designate like parts.

DETAILED DESCRIPTION

Figure 1:
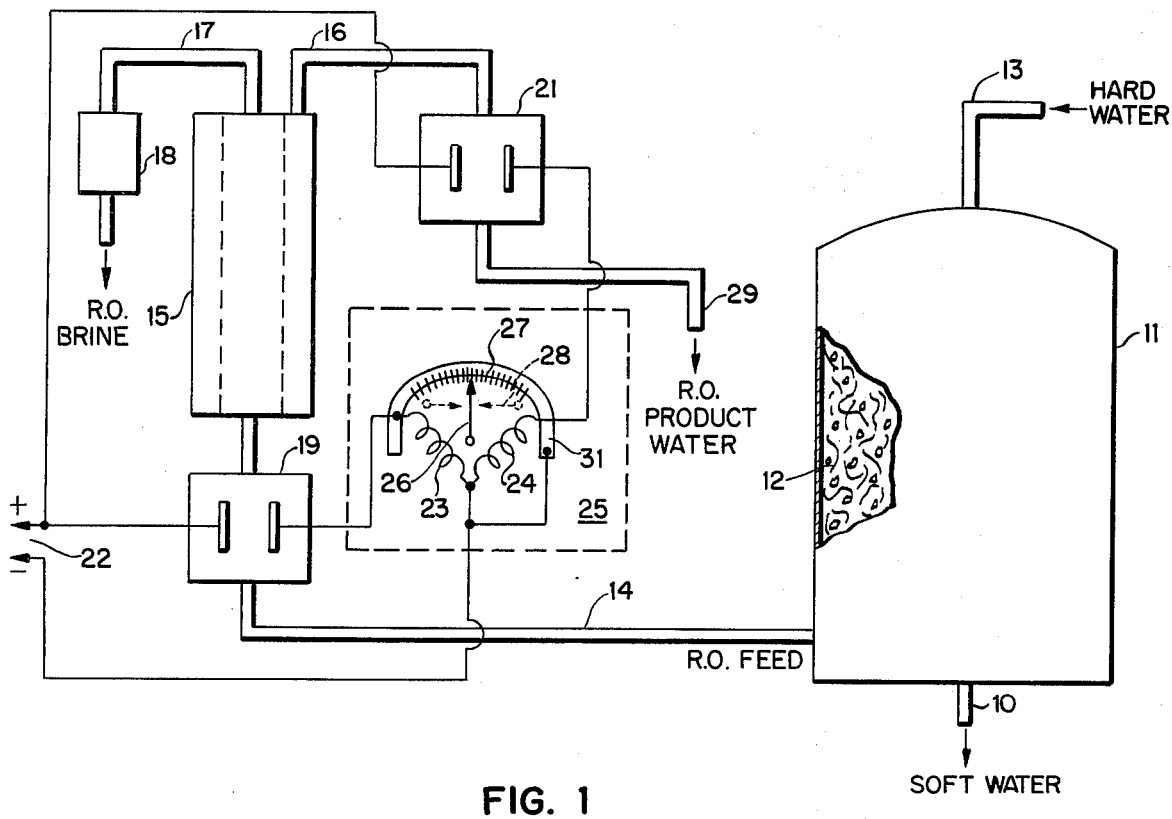

As represented in the drawing there is a tank 11 containing a column of ion exchange material such as zeolite resin 12 with an inlet pipe 13 for the feed of hard water to be treated. There is an outlet pipe 10 for delivering the softened water or product and a sample pipe 14 for supplying a sample to be tested.

In accordance with the invention a unit 15 is connected to the sample pipe 14 for discriminating between monovalent and divalent ions in the product by differentially rejecting such ions. A suitable ion discriminator takes the form of a reverse osmosis unit such as described in U.S. Pat. No. 3,133,137 of Loeb, Sourirajan and Weaver issued May 12, 1964. However, the reverse osmosis unit may be of any desired type such as a spiral wrap type cartridge. The tubular, hollow fiber, or flat plate and frame configuration may also be used. A standard cellulose acetate reverse osmosis membrane or other suitable membrane having different rejections for mono- and di-valent ions may be utilized.

The reverse osmosis unit 15 has an outlet pipe 16 for the product of the reverse osmosis unit and a discharge pipe 17 for the rejected brine stream with any suitable type of back pressure device 18 on the brine stream. A first through-flow conductivity cell 19 is connected in the sample line 14 in advance of the reverse osmosis unit 15 and a second through-flow conductivity cell 21 is connected in the product line 16 for the outflow from the reverse osmosis unit 15. Suitable means are employed for comparing the conductivities measured in the two conductivity cells 19 and 21. For example, as illustrated schematically, there may be a source of electrical current 22 connected in series with the conductivity cell 19 through one coil 23 of a conventional ratio meter and connected in series with the conductivity cell 21 through a second coil 24 of the ratio meter 25 having a pointer 26 cooperating with a scale 27 calibrated in some convenient scale.

Alternatively, the instrument 25 may be provided with contacts 28 and biasing means (not shown) for causing the contacts 28 to close only when the relationship between the currents flowing in the conductivity cells 19 and 21 reaches the value corresponding to water softener column exhaustion.

Although the conductivity detection elements 19 and 21 have been shown as flow type conductivity cells, the invention is not limited thereto and does not exclude the use of other suitable types of conductivity measuring elements such as screw-in or other type conductivity measurement devices. They may be composed of glass, epoxy or other materials or construction, whether or not temperature compensated.

The instrument 25 may be employed for actuating an alarm, recorders or various output devices (not shown).

OPERATION

The apparatus will operate efficiently at any pressure above the osmotic pressure of the feed solution. Typically this will be approximately 60 pounds per square inch. As shown, the ion discrimination apparatus 15 is installed so that its feed through the line 14 will be from a point slightly above the bottom of the softener column 12 so that total exhaustion of the zeolite softening resin can be anticipated. This feed will contain sodium ions as the primary cation, since the softener column acts to replace other cations with sodium. The rejection of a standard cellulose acetate reverse osmosis membrane toward sodium is normally 90%, and therefore the product water from outlet pipe 29 will have a conductivity approximately one tenth that of the water in the line 14 from the softener column 12. By suitable selection of cell constants the signals from the two cells 19 and 21 can be balanced in the instrument 25. Alternatively, the balance or zero point may be adjusted by suitable biasing means such as biasing springs or by selection of a suitable point on the scale 27 as the zero value.

It will be understood that in case the current source 22 is a direct current source and the magnetic field in which the coils 23 and 24 rotate is supplied by a permanent magnet 31, the coils 23 and 24 shown as crossed coils mounted upon a pivoted rotatable unit (not shown) will take up a position in which the tendency for each coil 23 and 24 to become aligned with the magnetic field will be balanced.

When the column 12 breaks through or becomes exhausted and calcium and magnesium ions are no longer replaced with sodium ions, the sodium content in the supply through sample line 14 to the reverse osmosis unit 15 decreases and the divalent ion content increases. The cellulose acetate membrane in the unit 15 has a rejection toward divalent ions of close to 99%, and therefore the amount of divalent ions in the product line 29 will be 1% or less of the feed. The amount of sodium in the product will also decrease, since the membrane rejects 90% of the feed concentration of sodium and the sodium content in the feed will decrease in proportion to the divalent increase. This will cause the conductivity meter to become unbalanced from its normal position, giving an indication of column breakthrough.

As an example, if water containing 500 ppm NaCl with 500 ppm $CaCl_2$ were softened, the product water would contain 1,026 ppm NaCl. Assuming the conductivities to be additive, the feed conductivity would be 1,000 $\mu$mhos/cm (NaCl) plus 1,100 $\mu$mhos/cm $CaCl_2$) = 2,100 $\mu$mhos/cm. The product conductivity would be 2,050 $\mu$mhos/cm. The feed water to the reverse osmosis unit 15 before the column is exhausted will contain 1,026 ppm NaCl (2,050 $\mu$mhos/cm). The reverse osmosis product water will contain 103 ppm NaCl (220 $\mu$mhos/cm), assuming a 90% rejection. When the column breaks through or is exhausted, the feed to the reverse osmosis unit will contain 500 ppm NaCl (1,000 $\mu$mhos/cm) and 500 ppm $CaCl_2$ (1,100 $\mu$mhos/cm). The sodium rejection will be 90%, but the calcium rejection will be 99%. Therefore, the reverse osmosis product water will contain 50 ppm NaCl (106 $\mu$mhos/cm) and 5 ppm $CaCl_2$ (15 $\mu$mhos/cm). The conductivity of this water will be 121 $\mu$mhos/cm, or an approximate 50% decrease, readily observable on standard conductivity equipment.

The novel use of a reverse osmosis membrane unit to separate hardness or divalent cations from sodium or monovalent cations, and measuring the difference in conductivity change as an indication of the presence of hardness, enables the hardness in water and softener exhaustion to be measured relatively inexpensively with rugged and reliable, durable equipment.

Thus, it becomes unnecessary to rely upon the use of ion selective electrodes, which are sensitive to fouling, breakage, etc. and require expensive monitoring equipment or to rely upon the use of a colorimetric analysis. Moreover, the arrangement of the invention is useful over the entire concentration range and is unaffected by a high background of sodium ion in the unsoftened water.

Although the conductivity cells 19 and 21 have been illustrated and described as mounted in lines 14 and 16, before and after the reverse osmosis unit 15, the invention is not limited thereto. The invention does not exclude mounting the conductivity cells 19 and 21 in lines 14 and 17 or in lines 16 and 17, for example. Thus, the conductivity cells may be used to monitor sample feed and brine, sample feed and water product of the reverse osmosis unit or product and brine.

Apparatus of the foregoing type is useful whenever it is necessary to discriminate between any ion concentrations, as long as the two different ions are rejected to different extents by the reverse osmosis membrane. This differing rejection may be achieved by using a different membrane or by using some chemical additive to the feed which will alter the rejections of the ions.

Moreover, the arrangement is useful for high conductivity waters as well as those of low conductivity.

Although a ratio-type instrument 25 has been illustrated in FIG. 1 and described in connection with the operation of that apparatus, it will be understood that the invention is not limited thereto and does not exclude the use of a differential type of device such as the differential relay 41 illustrated in FIG. 2, having opposing coils 42 and 43 in series with conductivity cells 19 and 21 respectively and acting differentially upon an armature carrying a movable contact 44 adapted to close a circuit to a stationary contact 45 to close an actuating circuit in a time switch 46 when the softener column becomes exhausted.

Figure 2:
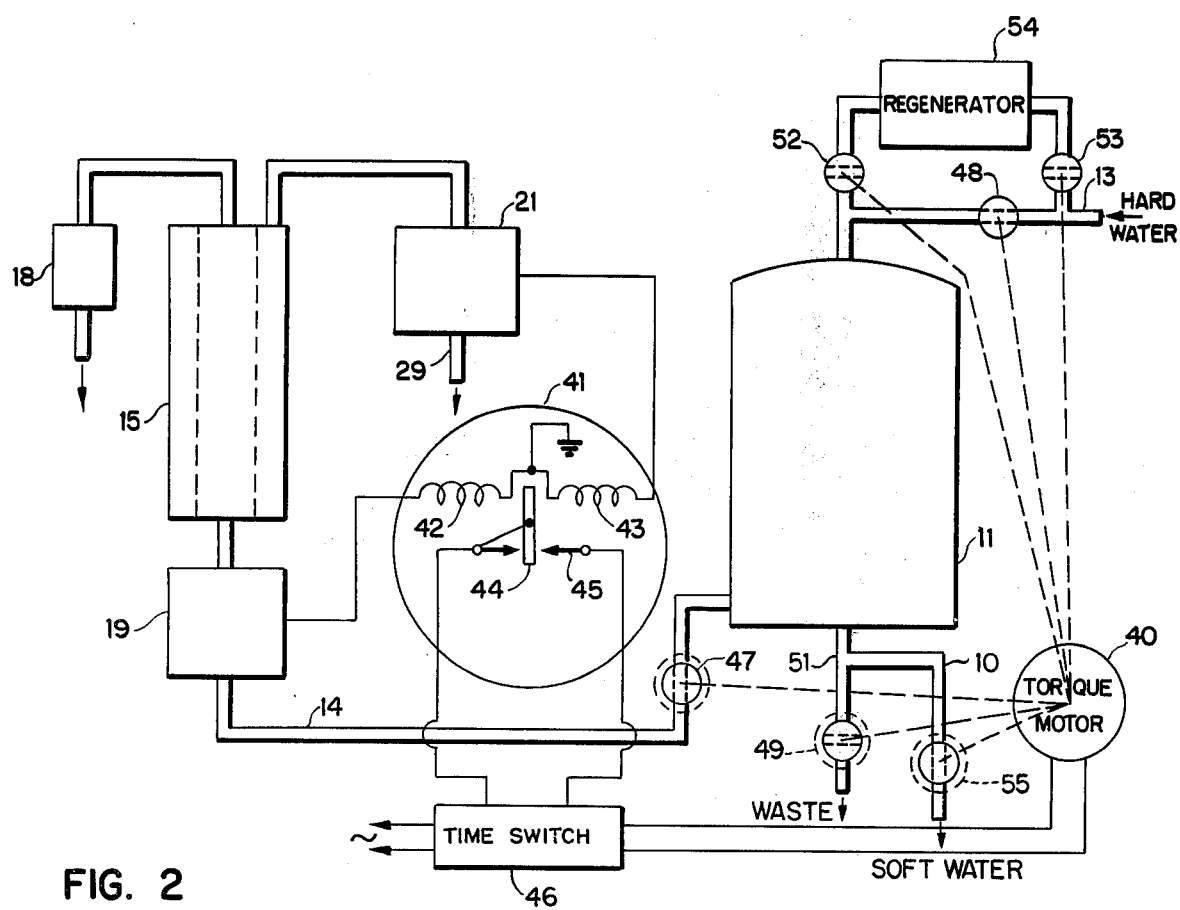

As shown in FIG. 2, the time switch 46 may be connected to actuate a torque motor 40 serving to reverse the positions of various valves in the water lines. During normal operation of the water softening system, the following valves are open: valve 47 in sample line 14, valve 48 in line 13 and valve 55 in the soft water output line 10; and the following valves are closed: valve 49 in waste discharge or purging line 51 from the tank 11, valves 52 and 53 bypassing the valve 48 and connecting the input line 13 and the tank 11 to a regenerator salt supply 54. When the time switch 46 is actuated by closure of the contacts 45 and 44, the torque motor 40 is energized to rotate each of the valves to its opposite condition so that water flows through the input line 13 through valve 53, regenerator 54, valve 52, tank 11, waste discharge pipe 51 and discharge valve 49 while valves 55 and 47 are closed to prevent delivery of salt water through the output line 10 and the sample line 14, and the valve 48 is closed to cause all of the feed water to flow through the regenerator 54. Then after the lapse of the time set by the time switch 46 determined by the characteristics of the system, regeneration ceases and the original valve connections are restored. If desired, the arrangement may be such as to delay the reopening of the valves 47 and 55 so as to flush the column 12 with clean water before restoring flow through the valve 55 and the product line 10.

While certain embodiments of the invention have been fully illustrated and described, it will be obvious to those skilled in the art that various modifications and alterations may be made therein and it is intended to cover all such modifications and alterations as may fall within the spirit and scope of the invention.

What is claimed is:

1. A method of determining the relative exhaustion of a sodium form water softener which comprises the steps of:

measuring the conductivity of a sample of the outflow of the water softener;

removing sodium and hardness ions from the sample at different rates downstream of said measuring;

measuring the conductivity of the sample downstream of said removal;

determining the ratio of said measurements; and determining said relative exhaustion from changes in said ratio.

2. The method of claim 1 including the step of:

applying forces proportional to said measurements to an indicating device to indicate said relative exhaustion.

3. The method of claim 1 for indicating breakthrough of the water softener including the step of:

indicating breakthrough when the change in said ratio of measurements exceeds a predetermined threshold level.

4. The method of claim 1 including the step of:

taking the sample of water to be measured upstream of the output of the water softener, whereby total exhaustion of the water softener may be anticipated.

5. The method of claim 4 for continuously operating a water softener in a nonexhausted condition, including the additional steps of:

applying forces proportional to said measurements to a switching device to maintain the switch in a first state during normal operation of the water softener, said forces causing the switch to change to a second state when the ratio of said measurements changes more than a predetermined threshold amount indicating anticipated breakthrough;

causing regeneration of the water softener to begin upon change to said second state;

maintaining regeneration for a predetermined time period thereafter.

6. The method of claim 1 wherein the difference in said removal rates is in the order of 10 to 1.

7. The method of claim 6 wherein the sodium ions and hardness ions are removed at the rates of approximately 90% and 99% respectively.

8. The method of claim 1 wherein the sodium and hardness ions are removed from the sample by applying the sample to a membrane exhibiting differential rejection.

9. The method of claim 8 wherein said differential rejection is accomplished by reverse osmosis.

10. Apparatus for determining the relative exhaustion of a sodium form water softener having a tank including ion exchange material in the flow path of the water to be softened, comprising:

a first flow-through cell for measuring the conductivity of water flowing therethrough connected to the tank to receive a sample of the water therein that has contacted the ion exchange material;

means connected to the downstream side of the first cell for removing sodium and hardness ions from the sample flowing therethrough at different rates;

a second flow-through cell for measuring the conductivity of water flowing therein connected to the downstream side of the ion removing means; and signal processing means connected to both conductivity cells to determine the relative exhaustion of the water softener by detecting changes in the ratio of the conductivities measured.

11. The apparatus of claim 10 wherein the signal processing means includes:

a member mounted for motion;

means connected to the first cell for applying a force to the member proportional to the conductivity measured by said first cell;

means connected to the second cell to apply a counterbalancing force to the member proportional to the conductivity measured by said second cell; and means for determining the relative exhaustion of the water softener as a function of the position of the movable member.

12. The apparatus of claim 10 for indicating breakthrough of the water softener wherein the signal processing means includes:

means connected to the cells to detect any change in the ratio of the measurements exceeding a predetermined threshold level.

13. The apparatus of claim 10 wherein the first flow cell is connected to the tank upstream of the outlet thereof whereby total exhaustion may be anticipated.

14. The apparatus of claim 13 wherein the signal processing means includes:

a member mounted for motion;

means connected to the first cell to apply a force to the member proportional to the conductivity measured by the first cell;

means connected to the second cell to apply a counterbalancing force to the member proportional to the conductivity measured by the second cell, said forces being balanced to maintain the member in a first state until a change in the ratio of the measurements exceeds a predetermined threshold level whereupon said forces maintain the member in a second state; and means connected to the member to cause regeneration of the water softener for a predetermined time period after the change to the second state.

15. The apparatus of claim 10 wherein the removal means includes a membrane across the flow path of the sample of water exhibiting differential rejection.

* * * * *